United States Patent [19]

Roychowdhury

[11] Patent Number: 4,480,035
[45] Date of Patent: Oct. 30, 1984

[54] PRODUCTION OF HYDROGEN

[76] Inventor: Sukomal Roychowdhury, 174 Heathecote Rd., Elmont, N.Y. 11003

[21] Appl. No.: 327,165

[22] Filed: Dec. 3, 1981

Related U.S. Application Data

[63] Continuation-in-part of Ser. No. 157,860, Jun. 9, 1980, abandoned.

[51] Int. Cl.³ .............................................. C12P 3/00
[52] U.S. Cl. .................................. 435/168; 435/813; 435/849
[58] Field of Search ............... 435/168, 166, 167, 253, 435/254, 209, 171, 801, 813, 849; 48/197 A, 197 FM; 210/603, 610

[56] References Cited

U.S. PATENT DOCUMENTS

| | | | |
|---|---|---|---|
| 663,623 | 12/1900 | Cameron | 48/197 A |
| 1,303,891 | 5/1919 | Harris | 48/197 FM |
| 1,777,449 | 10/1930 | Rath | 48/197 A X |
| 1,838,474 | 12/1931 | Buswell et al. | 435/167 X |
| 1,863,636 | 6/1932 | Quelch et al. | 48/197 FM |
| 1,990,523 | 2/1935 | Buswell et al. | 435/167 X |
| 2,029,702 | 2/1936 | Buswell et al. | 48/197 A |
| 2,429,589 | 10/1947 | Wiley | 435/167 |
| 3,383,309 | 5/1968 | Chandler | 48/197 A |
| 3,711,392 | 1/1973 | Metzger | 435/167 X |
| 3,764,475 | 10/1973 | Mandels et al. | 435/209 X |

Primary Examiner—R. B. Penland
Attorney, Agent, or Firm—Barry Evans

[57] ABSTRACT

A process for the production of hydrogen from glucose by innoculating a glucose solution with hydrogen producing bacteria to form hydrogen and carbon dioxide, separating the hydrogen from the carbon dioxide and conducting the hydrogen to storage. The glucose may be obtained from a cellulosic biomass by enzymatic hydrolysis or otherwise. The process may be continuously run in a fermentation tank with the continuous feed of cellulosic biomass.

1 Claim, No Drawings

PRODUCTION OF HYDROGEN

CROSS REFERENCE TO RELATED APPLICATION

This application is a continuation-in-part of U.S. patent application Ser. No. 157,860 filed June 9, 1980, now abandoned.

This invention relates to the production of hydrogen and more particularly to a process for the continuous production of hydrogen from glucose obtained from garbage.

It is amongst the primary objects of the invention to provide a practical and efficient process of both garbage disposal and hydrogen production.

It is another very important object of this invention to provide a method for converting glucose into hydrogen in high yields.

Other objects and advantages will become apparent from a reading of this specification.

Briefly stated, in one preferred form the invention contemplates a continuous process for the production of hydrogen from cellulosic material such as refuse, paper, vegetation, sewage and the like and consists of breaking the mass into particles, soaking the pulverized mass in a fungal enzyme broth to form a glucose syrup, adjusting the syrup to permit the decomposition of glucose by microbial activity, innoculating the syrup with hydrogen producing bacteria to produce hydrogen and carbon dioxide, drawing off and separating the hydrogen and carbon dioxide, conducting the hydrogen to storage while introducing more pulverized biomass into the system and repeating the process.

In its broadest form the invention is not dependent upon the use of garbage. The garbage merely serves as a cost free and unlimited source of biodegradable material from which glucose may be obtained. Glucose from whatever source will satisfy the demands of the invention.

DETAILED DESCRIPTION

The process may be practiced at any large municipal garbage facility where vast quantities of garbage are handled daily. Its practice would require at least one huge reactor comparable in size to the large "gas tanks" presently in use in most localities. The reactor serves as a fermentation vessel.

The refuse utilized in the process must be cellulosic in composition. This presents no problem because the bulk of the garbage collected is of this nature, i.e., paper, vegetation, kitchen wastes, sewage, etc.

At the onset there should be a separation of cellulosic from non-cellulosic materials such as metals, glass, plastics and the like. Additionally, the mass should be pulverized by grinding or shredding to facilitate the chemical conversions to follow.

In any event, a large quantity of pulverized cellulosic material is placed within the reactor and converted to glucose by enzymatic hydrolysis. This is accomplished by soaking the mass in a broth of fungel enzyme and permitting the mass to ferment. Trichoderma reesei, an aerobic cellulase producer, has been found to be surprisingly effective in this connection. The object, however, is to initially convert the biomass into glucose and although enzymatic hydrolysis would appear to be the most practical method at the present it is certainly not the only method that could be used to produce glucose.

Next and most important, the resultant glucose solution is adjusted to a pH of about 7, a glucose concentration of 0.5–20% and a temperature in the range of 30° to 60° C.

The solution is then innoculated with hydrogen producing bacteria to produce hydrogen and carbon dioxide in substantial quantities within a week. Hydrogen production should peak within a short time.

The following bacteria have been found to be strikingly effective, singly or in combination: *Citrobacter freundii; Enterobacter aerogenes; Escherichia coli;* Bacillus; Pseudomonas; Mixed culture bacteria.

Thereafter, the hydrogen and carbon dioxide are conducted from the reactor, the carbon dioxide being separated from the hydrogen by absorption and the hydrogen conducted to storage for use as a fuel.

Unusually good results have been obtained with yields of hydrogen in a range of 60 to 90%.

If hydrogen production is to be successful it is essential to provide a nutritive support system for the bacteria. A minimal salt solution and/or a Thioglycollate medium which have been found most advantageous in this respect. An example of the salt solution is as follows: (in gm/100 ml) $KH_2PO_4$, 1.5; $K_2HPO_4$, 1; NaCl, 1; $MgSO_4.7H_2O$. 0.7; $NH_4SO_4$, 4; Sodium citrate.2 $H_2O$, 0.5 An example of the Thioglycollate medium is as follows: (1% Difco in gm/100 ml) peptone, 2; NaCl, 0.25; Na thioglycollate, 0.05; 1-cystine, 0.05; agar, 0.075.

It may be seen that the entire reaction can essentially take place in one vessel and without the need of transferring the reactant mass. It may be further seen that once in operation, the process is both continuous and simultaneous, the feed of all essential materials being carried out in a continuous flow by suitable tubing, valving and control instruments.

EXAMPLE 1

Glucose Production 5 grams of grounded cellulosic waste matter was placed in a 3 necked flask. 100 c.c. of Trichoderma enzyme was added in the flask and shaken thoroughly. A small piece of a magnatic bar was placed inside the flask to stirr the material when placed on top of a stirrer. The three necks of the flask was fitted with 3 different connections.

One neck was fitted with a metal probe, connected to an automatic tempatature controller. Middle neck was fitted with a thermometer and pH electrode; the third neck was fitted with a delivery tube to lead the emerging gas to a burette, which was inverted over water filled beaker.

The flask thus fitted was placed on a heating mantle and finally placed on a mechanical stirrer. The temperature was kept at 50° C. and pH at 4.8 for saccharification. Once glucose was made after 48 hours, it was cooled and diluted with previously made inorganic salt solution, to make up the concentration of the solution from 0.5–20% according to the need. Also 1% thioglycollate medium was added to the solution. A buffer solution was also added to maintain the pH from changing. All fittings and connections were then rechecked and made ready for the next step to produce gas.

Gas Production Stage

At first, the tempature was raised to 37° C. and pH was adjusted to 6.5–7. A specially cultured *Citrobacter freundii* bacteria (2 cc–3 cc inoculum) was inoculated inside the flask. After about 48 hours of incubation hydrogen and carbon dioxide gas was evolved.

| Results | |
|---|---|
| % Hydrogen | % Carbon dioxide |
| 45 | 40 |

EXAMPLE 2

The experimental procedure was same as example 1. The only difference was the inoculum.

The inoculum in example 2 was *Escherichia coli* and 2 cc to 3 cc of the freshly made bacterial inoculum was inoculated into the flask.

| Results | |
|---|---|
| % Hydrogen | % Carbon dioxide |
| 54% | 34% |

EXAMPLE 3

The experimental procedure was also same as example 1. The only difference was the inoculum. In this example 1 cc of *Citrobacter freundii*, 1 cc of E. coli, 1 cc of *Enterobacter aerogenes*, 1 cc Bacillus and 1 cc Pseudomonas was inoculated into the mentioned flask.

| Results | |
|---|---|
| % Hydrogen | % Carbon dioxide |
| 64 | 22 |

EXAMPLE 4

The experimental procedure was similar to example 1. The differences were as follows:
(a) The inoculum (mixed culture of bacteria)
(b) Temperature 55° C.
(c) The concentration of the glucose solution in the flask was 5%.

The inoculum used in this experiment was a mixed culture of bacteria. The primary source of the culture was from sewage sludge. The inoculum was specially treated and adopted to make a specific high yielding hydrogen producers. About 4 cc of this inoculum was inoculated into the glucose solution of the fuusk. Temperature was maintained at 55° C. and pH was kept at 7 by using buffer solution. After about 48 hours of incubation hydrogen and carbon dioxide gas was evolved.

| Results | |
|---|---|
| % Hydrogen | % Carbon dioxide |
| 87 | 10 |

I claim:
1. A continuous process for the production of hydrogen from a cellulose material by microbial fermentation comprising the steps of:
  (a) enzymatically hydrolyzing said cellulose material to produce a glucose solution
  (b) maintaining said glucose solution and a nutritive support medium comprising a minimal salt solution and thioglycolate in a fermentation vessel at a pH of about 7 and at a temperature in the range of 30° to 60° C., said glucose being 1.5 to 20% by weight of the solution, and said solution being thereby amenable to decomposition by microbial metabolic action;
  (c) inoculating said glucose solution with a hydrogen producing bacteria selected from the group consisting of: *Citrobacter freundii, Enterobacter aerogenes, Escherichia coli,* Bacillus and pseudomona,
  (d) permitting said inoculated glucose solution to incubate and produce hydrogen and carbon dioxide; and
  (e) separating the hydrogen and carbon dioxide from said solution whereby hydrogen is produced in a substantial yield.

* * * * *